(12) United States Patent
Lidgren

(10) Patent No.: US 7,387,613 B2
(45) Date of Patent: Jun. 17, 2008

(54) DEVICE FOR NON-INVASIVE ULTRASOUND TREATMENT OF DISC DISEASE

(75) Inventor: Lars Åke Alvar Lidgren, Lund (SE)

(73) Assignee: Ultrazonix DNT AB, Limhamn (SE)

( * ) Notice: Subject to any disclaimer, the term of this patent is extended or adjusted under 35 U.S.C. 154(b) by 0 days.

(21) Appl. No.: 10/333,159

(22) PCT Filed: Jul. 16, 2001

(86) PCT No.: PCT/SE01/01625

§ 371 (c)(1),
(2), (4) Date: Mar. 11, 2003

(87) PCT Pub. No.: WO02/05896

PCT Pub. Date: Jan. 24, 2002

(65) Prior Publication Data

US 2003/0163066 A1    Aug. 28, 2003

(30) Foreign Application Priority Data

Jul. 17, 2001    (SE) .................................. 0002677-3

(51) Int. Cl.
*A61H 1/00*    (2006.01)
*A61H 1/02*    (2006.01)
*A61H 5/00*    (2006.01)
*A61B 8/00*    (2006.01)

(52) U.S. Cl. .......................................... 601/3; 600/439

(58) Field of Classification Search ................. 600/439, 600/407, 103; 601/2–4; 604/20–22; 606/27, 606/28; 128/899

See application file for complete search history.

(56) References Cited

U.S. PATENT DOCUMENTS

| 5,150,712 | A |   | 9/1992  | Dory                         |
|-----------|---|---|---------|------------------------------|
| 5,433,739 | A | * | 7/1995  | Sluijter et al. ........... 607/99 |
| 5,443,068 | A |   | 8/1995  | Cline et al.                 |
| 5,471,988 | A | * | 12/1995 | Fujio et al. ............. 600/439 |
| 5,526,814 | A | * | 6/1996  | Cline et al. ............. 600/411 |
| 5,769,790 | A | * | 6/1998  | Watkins et al. .......... 600/439 |
| 5,984,881 | A | * | 11/1999 | Ishibashi et al. .......... 601/2 |
| 6,019,724 | A | * | 2/2000  | Gronningsaeter et al. ... 600/439 |

(Continued)

FOREIGN PATENT DOCUMENTS

EP    0872262    10/1998

(Continued)

*Primary Examiner*—Matthew F. Desanto
(74) *Attorney, Agent, or Firm*—Ladas & Parry LLP

(57) ABSTRACT

A device for non-invasive ultrasound treatment of disc disease. This device includes a therapeutic ultrasound transducer which is provided for treatment of the disc, preferably nucleus pulposus, of a patient by generating an ultrasonic field, the temperature focus (F) of which is located in the disc, preferably nucleus pulposus, for heating thereof. The therapeutic ultrasound transducer is of a "phased array"-type and a diagnostic ultrasound transducer is provided to determine the acoustic properties of the patient's tissue. An optical navigating device including at least one diagnostic camera and at least one signal receiving and/or signal sending unit is adapted to send or transmit signals to and/or receive reflected or other signals from position transmitters on a reference device and on the therapeutic ultrasound transducer. A computer is provided with at least one computer program which is designed for calculations in connection with settings of the device.

37 Claims, 2 Drawing Sheets

Figure 1:
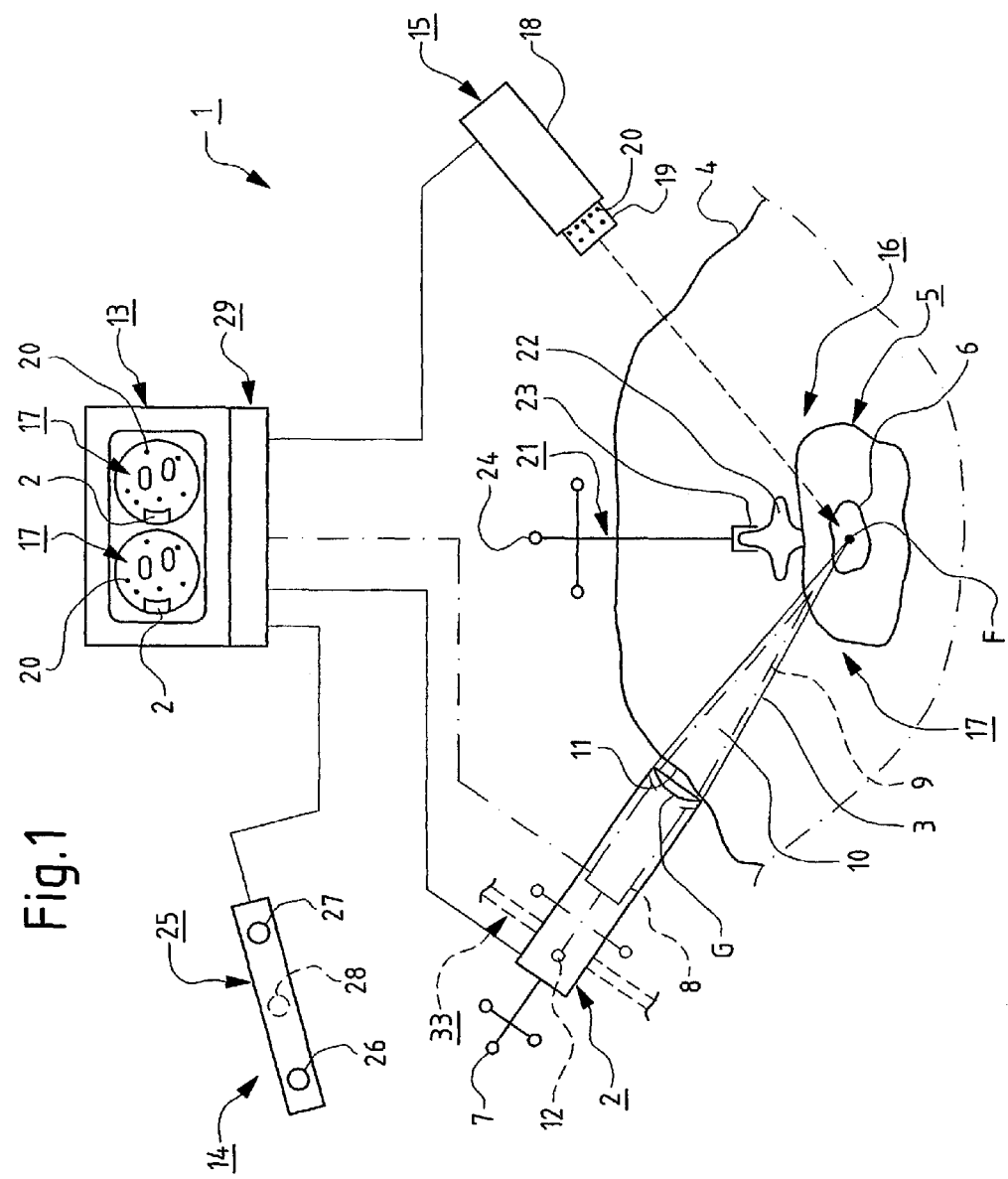

U.S. PATENT DOCUMENTS 6,042,556 A * 3/2000 Beach et al. .................... 601/3
6,254,553 B1 * 7/2001 Lidgren et al. ................. 601/3
6,488,639 B1 * 12/2002 Ribault et al. .................. 601/2
6,511,444 B2 * 1/2003 Hynynen et al. ............... 601/2

FOREIGN PATENT DOCUMENTS

WO    WO 9958196   * 11/1999

* cited by examiner

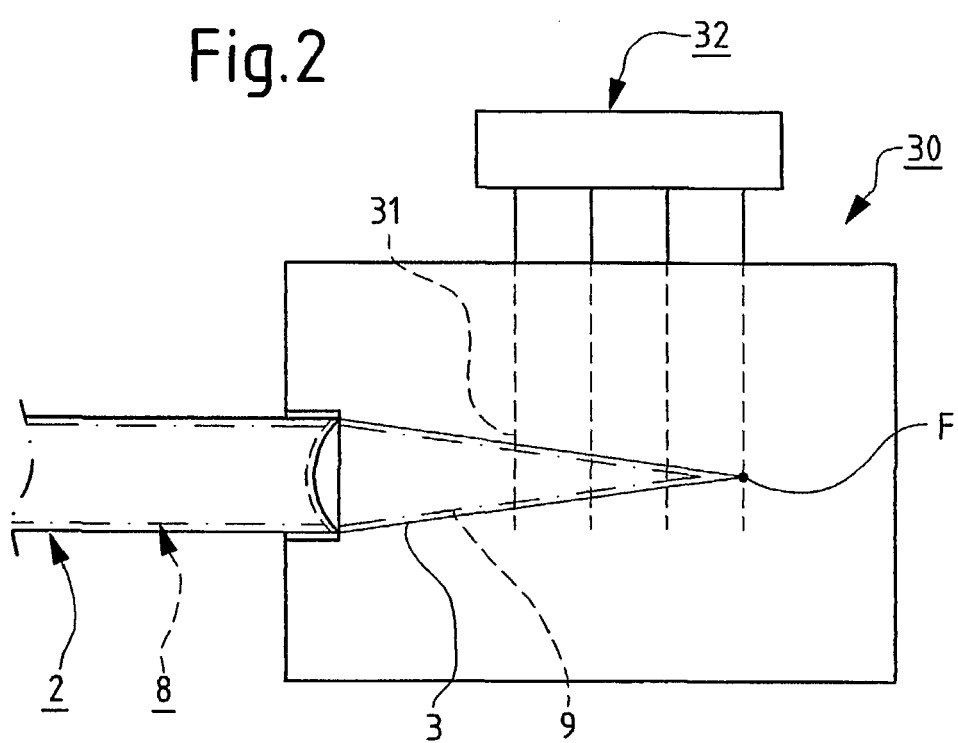

DEVICE FOR NON-INVASIVE ULTRASOUND TREATMENT OF DISC DISEASE

BACKGROUND OF THE INVENTION

The present invention relates to a device for non-invasive ultrasound treatment of disc disease, wherein at least one therapeutic ultrasound transducer is provided for treatment of the disc, preferably nucleus pulposus, of a patient by generating by means of said therapeutic ultrasound transducer an ultrasonic field, the temperature focus of which is located in the disc, preferably nucleus pulposus, for heating thereof, and wherein the therapeutic ultrasound transducer is of a "phased-array"-type for being able to vary the distance between the transmitter element of the therapeutic ultrasound transducer and the temperature focus of its ultrasonic field.

The intervertebral disc consists of an outer fibrous tissue ring, anulus fibrosus, and an inner, more viscous part, nucleus pulposus. The disc functions as a shock absorber and if anulus fibrosus breaks, e.g. a small fissuring, disc matter may find its way out and cause a compression of nerve roots and induce an inflammatory reaction.

Prolapsed intervertebral discs have been treated surgically since the thirties by removal of the displaced disc matter and/or a part of the bulging disc. Later, the surgical treatment has developed towards less invasive operations and now, microscopes and percutaneous techniques are used for removing disc matter. An alternative method for surgical treatment is chemonucleolys, where the enzyme chymopapain is injected into nucleus pulposus, the central part of the disc. The enzyme polymerizes the long proteoglycan chains in nucleus pulposus with subsequent loss of the hygroscopicity. This reduces the volume and pressure in nucleus pulposus and the bulging part of the disc, which explains the pain relief patients with sciatica experience after chemonucleolys. The method has proven to give pain relief in 75 per cent of the cases and has a well documented cost efficiency. Unfortunately, the method has caused serious allergic reactions in about 1 per cent of the cases. Next step in the development could be a non-invasive treatment or therapy of prolapsed intervertebral discs, which preferably should be painless, avoid the risk for infections and carried through ambulatory.

A method for thermotherapy and coagulation of tissue involves use of focused ultrasound with high intensity. The ultrasouond pass well through soft tissue and can be focused on remote spots within a surface of a few millimeters. The energy absorption in the tissue increases the temperature with a sharp temperature gradient such that the boundaries of the treated volume are clearly limited without causing any damages on the surrounding tissue (U.S. Pat. No. 5,291,890, U.S. Pat. No. 5,501,655). Ultrasound treatment or therapy of prolapsed intervertebral discs is previously known (EP 0 872 262).

Heat treatment or thermotherapy of discs has proven successful in a method called IDET (U.S. Pat. No. 6,073,051, U.S. Pat. No. 6,007,570, U.S. Pat. No. 5,980,504). The method has as its aim to insert a catheter into the disc by means of a cannula. Farthest out on the catheter there is a spool which is heated by applying a radio frequency voltage thereon (U.S. Pat. No. 6,785,705). The heat is increased to about 90° C. in nucleus pulposus where the heating element of the catheter has been located and treatment or therapy is carried through for about 15 minutes.

Surgery with focused ultrasound has several advantages compared with other thermal techniques. In the first place, it is non-invasive, secondly, focus can be made movable and thirdly, the energy can be supplied in a few seconds. The limitation of ultrasound is its absorption in bone and its poor penetration through gas-filled passages. Clinical applications of ultrasound surgery are today mostly used in ophtalmic surgery, urology and oncology. The effect of ultrasound can be divided into thermal and non-thermal effects.

The thermal effects of ultrasound are caused by absorption of ultrasound in the tissue. This leads to a temperature increase which is dependent on the parameters of the ultrasound (frequency and intensity) and the acoustic properties of the tissue. The absorption of ultrasound in musculoskeletal tissues increases with the apatite and protein content, which means high absorption in bone, cartilage, tendons and ligaments. Water however, has a low ultrasound absorption capacity and can for this reason be used as an acoustic medium between the ultrasound transducer and the tissue. Higher absorption can be expected in anulus fibrosus (high collagen content) than in nucleus pulposus (high water content). This will lead to higher temperatures in the outer part of the intervertebral disc than in the central part. In order to avoid that the temperature in anulus fibrosus exceeds detrimental level at the same time as the temperature in nucleus pulposus reaches a sufficient level, the ultrasound can be transmitted from several ultrasound sources. In this manner, the fields will overlap each other and increase the effect in nucleus pulposus at the same time as the intensity in the surrounding tissue including anulus fibrosus can be kept low.

BRIEF SUMMARY OF THE INVENTION

The object of the present invention has been to facilitate, at the above-mentioned devices, location of the temperature focus of the ultrasonic field of the ultrasound transducer on a desired point in the disc, preferably in nucleus pulposus. This is arrived at according to the invention by means of a device having the characterizing features of subsequent claim 1.

By means of the device defined in the claims, it is achieved that the temperature focus of the ultrasonic field of the therapeutic ultrasound transducer can be located and maintained on the desired point in the disc, preferably in nucleus pulposus.

BRIEF DESCRIPTION OF DRAWING FIGURES

The invention will be further described below with reference to the accompanying drawings, in which FIG. 1 schematically illustrates a structural embodiment of the device according to the invention; and FIG. 2 schematically illustrates a calibrating device which may form part of a device according to FIG. 1.

DETAILED DESCRIPTION OF THE PREFERRED EMBODIMENTS

The treatment device 1 schematically illustrated in FIG. 1 is adapted to generate, by means of one or more therapeutic ultrasound transducers 2 (so called therapeutic transducers), one or more ultrasonic fields 3, the temperature focus F of which is intended to be located in the intervertebral disc 5, preferably in nucleus pulposus 6, of the patient 4 for treatment thereof, in FIG. 1, only one therapeutic ultrasound transducer 2 is illustrated, but there may be several transducers as in e.g. EP 0 872 262.

The therapeutic ultrasound transducer 2 comprises a plurality of, preferably three or more position transmitters 7 for determining its position.

In more detail, the therapeutic ultrasound transducer 2 is adapted to cause a local temperature increase in nucleus pulposus 6 so that enzymes such as collagenase present in the disc 5, are activated and cause decomposition of collagen and proteoglycanes, which results in shrinking of nucleus pulposus 6 primarily because of less hygroscopicity. The therapeutic ultrasound transducer 2 can transmit its ultrasonic field 3 dorsolaterally from several different ports simultaneously. For being able to vary the focal distance of the therapeutic ultrasound transducer 2, i.e. the distance between its transmitter element G and the temperature focus F, said therapeutic ultrasound transducer 2 must be of the "phased array"-type, including several small piezoelectric elements. By excitation of these elements with different time delays, a focused ultrasonic field 3 is generated.

The treatment device 1 further comprises a diagnostic ultrasound transducer 8. This is adapted to generate an ultrasonic field 9 for determining the acoustic properties of the patient's tissue 10 between the area 11 on the patient for location of the therapeutic ultrasound transducer 2 during treatment and the disc 5, preferably nucleus pulposus 6, to be treated. This "time of flight"-measurement with the diagnostic ultrasound transducer 8 is carried through for determining the distance between said area 11 and nucleus pulposus 6 as well as the thickness of the tissue and of the different issue layers.

The tissue 10 passed consists in said order of skin, fat, muscles and anulus fibrosus. This information is needed to correct differences in size and tissue configuration of various patients, since the attenuation of the ultrasound is different in different types of tissue.

The diagnostic ultrasound transducer 8 comprises a plurality of, preferably three or more position transmitters 12 for determining its position and it is provided to generate an image of said tissue 10 in a monitor 13.

The treatment device 1 also comprises an optical navigating device 14 to navigate the therapeutic ultrasound transducer 2 (U.S. Pat. No. 5,772,594). This optical navigating device 14 comprises at least one diagnostic camera 15 which is adapted to produce at least one picture or image of the anatomic structure 17 of the treatment area 16 in the monitor 13. The diagnostic camera may be an X-ray camera 18 taking two pictures of the anatomic structure 17 of the treatment area 16 from different directions with preferably a 90° intermediate angle and showing these in the monitor 13. At the optical navigating device 14, the X-ray camera 18 is used together with an optical analogue-digital-converter for obtaining a real time image or picture in the monitor 13 of the position and direction of the therapeutic ultrasound transducer 2 (U.S. Pat. No. 6,021,343, U.S. Pat. No. 5,834,759, U.S. Pat. No. 5,383,454).

The X-ray camera 18 comprises a calibrating device 19—e.g. a calibrating hood—which is located in front of the objective of the X-ray camera 18 and having markers 20 the mutual distance of which is known. The markers 20 may be round and consist e.g. of tantalum.

The optical navigating device 14 further comprises a reference device 21 which is provided to be attached to the spinous process 23 of a vertebra 22 or in a corresponding position such that it gets a determined or fixed position relative to the treatment area 16. The reference device 21 has several position transmitters 24, namely preferably at least three, and these may consist of tantalum.

Furthermore, the optical navigating device 14 comprises a signal receiving and/or signal sending unit 25. This includes a suitable number of signal receivers 26, 27 for receiving reflected or other signals from the position transmitters 7, 12 and 24 of the therapeutic ultrasound transducer 2, the diagnostic ultrasound transducer 8 and the reference device 21 respectively. The signal receiving and/or signal sending unit 25 may eventually comprise one or more signal transmitters 28 for sending or transmitting signals to said position transmitters 7, 12 and 24, which are provided to receive these signals.

The signals transmitted by the position transmitters 7, 12 and 24 may e.g. be in the form of infrared light and the signal receivers 26, 27 may in such case be receivers of infrared light.

The treating device 1 further comprises a computer 29 with at least one computer program or software which is designed to calculate a suitable setting of the transmitter element G of the therapeutic ultrasound transducer 2, based on the acoustic properties determined by the diagnostic ultrasound transducer 8, such that the temperature focus F of the ultrasound field 3 of the therapeutic ultrasound transducer 2 can be brought to appear in the disc 5, preferably in nucleus pulposus 6, to be treated.

Said program or software may alternatively, or in combination with said setting of the therapeutic ultrasound transducer 2, be provided to calculate the position of the temperature focus F of the ultrasonic field 3 of the therapeutic ultrasound transducer 2 relative to said therapeutic ultrasound transducer 2, based on said acoustic properties and the setting of the therapeutic ultrasound transducer 2 in view of its focusing properties, so that the therapeutic ultrasound transducer 2 by means of said optical navigating device 14 can be positioned such that said temperature focus F appears in the disc 5, preferably nucleus pulposus 6, to be treated.

The computer 29 may be provided with a program (software) which is designed to calculate the effect of the ultrasonic field 3 of the therapeutic ultrasound transducer 2 in its temperature focus F based on the acoustic properties determined by the diagnostic ultrasound transducer 8, such that the temperature increase in nucleus pulposus 6 caused by the therapeutic ultrasound transducer 2, can be determined.

In the treatment device 1 there may also be included a calibrating unit 30 for calibrating (a) the position of the temperature focus F of the therapeutic ultrasound transducer 2 relative to its transmitter element G, and (b) the heating effect in said temperature focus F generated by said therapeutic ultrasound transducer 2. The calibrating unit 30 has similar acoustic properties as human tissue and contains a plurality of thermoelements 31 by means of which the position and effect on said temperature focus F can be measured for calibration. The thermoelements 31 are connected to a schematically illustrated measure instrument 32.

Prior to treatment of the disc 5, preferably nucleus pulposus 6, the reference device 21 is located on the patient's 4 vertebra 22 and the therapeutic ultrasound transducer 2 as well as the diagnostic ultrasound transducer 8 are calibrated in the calibrating unit 30. Then, a tissue analysis is made by means of the diagnostic ultrasound transducer 8, which preferably is navigated by means of the optical navigating device 14 while its position transmitter 12 cooperates through signals with the signal receivers 26, 26. A tissue image generated by the diagnostic ultrasound transducer 8 can be produced on the monitor 13, and the values of the tissue measured with said diagnostic ultrasound transducer 8 are used for setting the focal distance and effect of the therapeutic ultrasound transducer 2.

Two X-ray pictures are taken of the patient's 4 anatomic structure 17 at the disc 5 and these X-ray pictures are shown on the monitor 13. On these X-ray pictures, the position of the position transmitters 24 of the reference device 21 relative to the disc 5 may then be determined by means of the markers 20 of the calibrating device 19.

During treatment of the disc 5, preferably nucleus pulposus 6, the therapeutic ultrasound transducer 2 is navigated by means of the signal receiving or signal sending unit 25, whereby the navigation is presented in the X-ray pictures or images on the monitor 13. This is accomplished while the position transmitters 7 of the therapeutic ultrasound transducer 2 cooperate through signals with the signal transmitters 26 of the signal receiving or signal sending unit 25. By means of said navigation, the therapeutic ultrasound transducer 2 can be positioned such that the temperature focus F of its ultrasonic field 3 will lie in the disc 5, preferably nucleus pulposus 6. The temperature in the temperature focus F preferably exceeds 45° C.

The treatment can be automatically interrupted if the patient 4 moves to an incorrect position relative to the therapeutic ultrasound transducer 2 or vice versa.

The invention is not limited to the embodiment described above, but may vary within the scope of the following claims. Thus, the treated disc 5 may e.g. be any disc in the body.

The diagnostic camera 15 may be a computerized tomography (CT) scanner which is provided to produce images of said anatomic structure 17 and these images can be processed in a computer program or software for obtaining a 3D-image in the monitor 13.

The therapeutic ultrasound transducer 2 may be provided to be positioned manually or be located on a positioning device 33 for positioning thereof relative to the disc 5 to be treated.

It should also be mentioned that the signal receiving or signal sending unit 25 of the optical navigating device 14 may be an X-ray device.

The invention claimed is:

1. Device for non-invasive ultrasound treatment of disc disease, comprising:

at least one therapeutic ultrasound transducer for treatment of the disc of a patient by generating by means of said at least one therapeutic ultrasound transducer an ultrasonic field, the temperature focus of which is adapted to be focused in the disc for heating thereof, and wherein the at least one therapeutic ultrasound transducer is of a "phased array"-type for being able to vary the distance between the transmitter element of the at least one therapeutic ultrasound transducer and the temperature focus of the ultrasonic field, a diagnostic ultrasound transducer to determine the acoustic properties of the patient's tissue between the location of the at least one therapeutic ultrasound transducer during the treatment and the disc to be treated, and a computer which is configured to calculate, based on the acoustic properties determined by the diagnostic ultrasound transducer, the distance between the area on the patient and the disc as well as the thickness of the patient's tissue and of the different tissue layers, and to make correction for differences in size and tissue configuration in order to take the different attenuation of the ultrasonic field in different types of tissue into account, and to control the temperature focus of the ultrasonic field of the at least one therapeutic ultrasound transducer by controlling time delays for excitation of piezoelectric elements of the at least one therapeutic ultrasound transducer, wherein the at least one therapeutic ultrasound transducer is positioned in relation to the disc to be treated, dependent on the acoustic properties determined by the diagnostic ultrasound transducer, wherein the transmitter element of the at least one therapeutic ultrasound transducer is set dependent on the correction for differences in size and tissue configuration such that the temperature focus of the ultrasonic field of the at least one therapeutic ultrasound transducer can be brought to appear in the disc to be treated.

2. Device according to claim 1, wherein the at least one therapeutic ultrasound transducer cooperates with an optical navigating device comprising at least one diagnostic camera which is adapted to produce at least one picture or image of the anatomic structure of the treatment area within which the disc to be treated is located.

3. Device according to claim 2, wherein the at least one diagnostic camera is an X-ray camera.

4. Device according to claim 3, wherein the X-ray camera comprises a calibrating device with markers which are adapted to determine the position of the anatomic structure of the treatment area displayed in a monitor.

5. Device according to claim 4, wherein the monitor is provided to display two X-ray photographs of said anatomic structure taken with the X-ray camera from two different locations.

6. Device according to claim 2, wherein the at least one diagnostic camera is a computerized tomography (CT) scanner which is provided to produce images of the anatomic structure at the patient's disc, said images being processed in a computer program for obtaining a 3D-image in a monitor.

7. Device according to claim 2, wherein the optical navigating device comprises at least one signal receiving and signal sending unit which is adapted to send or transmit signals to and receive reflected or other signals from position transmitters on a) a reference device which has a set position relative to the disc, and b) the at least one therapeutic ultrasound transducer such that the position thereof relative to said treatment area can be determined.

8. Device according to claim 7, wherein the diagnostic ultrasound transducer comprises position transmitters which cooperate with the signal receiving and signal sending unit.

9. Device according to claim 7, wherein the signal receiving and signal sending unit is provided to receive and send signals in the form of infrared light and that said position transmitters are provided to send and receive signals in the form of infrared light.

10. Device according to claim 7, wherein the reference device is capable of being attached to a vertebra in the patient's vertebral column, preferably to the spinous process of said vertebra.

11. Device according to claim 7, wherein the reference device comprises position transmitters consisting of metallic balls.

12. Device according to claim 7, wherein the signal receiving and signal sending unit of the optical navigating device consists of at least one X-ray device.

13. Device according to claim 1, wherein the computer is provided with at least one program which is designed to calculate a suitable setting of the transmitter element of the at least one therapeutic ultrasound transducer, based on the acoustic properties determined by the diagnostic ultrasound transducer, such that the temperature focus of the ultrasonic field of the at least one therapeutic ultrasound transducer can be brought to appear in the disc to be treated, whereby said program alternatively, or in combination with said setting of the at least one therapeutic ultrasound transducer, can be provided to calculate the position of the temperature focus of the ultrasonic field of the at least one therapeutic ultrasound transducer relative to said at least one therapeutic ultrasound transducer, based on said acoustic properties and the setting of the at least one therapeutic ultrasound transducer in view of its focusing properties, so that the at least one therapeutic ultrasound transducer by means of said optical navigating device can be positioned such that said temperature focus appears in the disc to be treated.

14. Device according to claim 13, wherein the computer is provided with at leas tone computer program which is designed to calculate the heating effect of the ultrasonic field of the at least one therapeutic ultrasound transducer in its temperature focus based on the acoustic properties determined by the diagnostic ultrasound transducer.

15. Device according to claim 1, wherein the diagnostic ultrasound transducer is provided to determine the thickness of different layers of said tissue for determining the acoustic properties thereof.

16. Device according to claim 1, wherein the diagnostic ultrasound transducer is provided to produce a picture or image of said tissue.

17. Device according to claim 1, wherein the diagnostic ultrasound transducer and the at least one therapeutic ultrasound transducer are the same unit.

18. Device according to claim 1, wherein the at least one therapeutic ultrasound transducer is provided to be positioned manually be means of calculated determination of the temperature focus of the ultrasonic field of said at least one therapeutic ultrasound transducer relative to the transmitter element of the at least one therapeutic ultrasound transducer.

19. Device according to claim 1, wherein the at least one therapeutic ultrasound transducer is provided on a positioning device for positioning thereof relative to the disc to be treated.

20. Device according to claim 1, wherein the at least one therapeutic ultrasound transducer provides a temperature focus that exceeds 45° C.

21. Device according to claim 1, wherein a calibrating device is provided for calibrating the effect emitted by the at least one therapeutic ultrasound transducer in the temperature focus of said at least one therapeutic ultrasound transducer and/or the position of said temperature focus relative to the transmitter element of the at least one therapeutic ultrasound transducer.

22. Method for non-invasive ultrasound treatment of disc disease, comprising the steps of:
  providing at least one therapeutic ultrasound transducer for treatment of the disc of a patient;
  generating by means of said at least one therapeutic ultrasound transducer an ultrasonic field, the temperature focus of which is located in the disc for heating thereof;
  varying the distance between the transmitter element of the at least one therapeutic ultrasound transducer and the temperature focus of its ultrasonic field by means of said at least one therapeutic ultrasound transducer that is of a "phased array"-type;
  determining, by means of a diagnostic ultrasound transducer, the acoustic properties of the patient's tissue between the least one therapeutic ultrasound transducer during the treatment and the disc to be treated,
  calculating, by means of a computer and based on the determined acoustic properties, the distance between the area on the patient and the disc as well as the thickness of the patient's tissue and of the different tissue layers;
  correcting for differences in size and tissue configuration in order to take the different attenuation of the ultrasonic field in different types of tissue into account,
  positioning the at least one therapeutic ultrasound transducer in relation to the disc to be treated, dependent on the acoustic properties determined by the diagnostic ultrasound transducer, and
  setting the transmitter element of the at least one therapeutic ultrasound transducer dependent on the correction for differences in size and tissue configuration by controlling time delays for excitation of piezoelectric elements of the at least one therapeutic ultrasound transducer such that the temperature focus of the ultrasonic field of the at least one therapeutic ultrasound transducer is brought to appear in the disc to be treated.

23. Method according to claim 22, further comprising the step of cooperating, by means of the at least one therapeutic ultrasound transducer, with an optical navigating device comprising at least one diagnostic camera which is adapted to produce at least one picture or image of the anatomic structure of the treatment area within which the disc to be treated is located.

24. Method according to claim 23, further comprising the step of providing the optical navigating device with at least one signal receiving and signal sending unit which is adapted to send or transmit signals to and receive reflected or other signals from position transmitters on
  a) a reference device which has a set position relative to the disc, and
  b) the at least one therapeutic ultrasound transducer such that the position thereof relative to said treatment area can be determined.

25. Method according to claim 24, further comprising the steps of receiving and sending, by means of the signal receiving and signal sending unit, signals in the form of infrared light and by means of said position transmitters sending and receiving signals in the form of infrared light.

26. Method according to claim 24, further comprising the step of attaching the reference device to a vertebra in the patient's vertebral column, preferably to the spinous process of said vertebra.

27. Method according to claim 23, further comprising the step of producing, by means of the at least one diagnostic camera, images of the anatomic structure at the patient's disc, said images being processed in a computer program for obtaining a 3D-image in a monitor.

28. Method according to claim 22, further comprising the steps of calculating, by means of a computer provided with at least one program, a suitable setting of the transmitter element of the at least one therapeutic ultrasound transducer based on the acoustic properties determined by the diagnostic ultrasound transducer, such that the temperature focus of the ultrasonic field of the at least one therapeutic ultrasound transducer can be brought to appear in the disc to be treated, whereby said program alternatively, or in combination with said setting of the at least one therapeutic ultrasound transducer, can be provided to calculate the position of the temperature focus of the ultrasonic field of the at least one therapeutic ultrasound transducer relative to said at least one therapeutic ultrasound transducer, based on said acoustic properties and the setting of the at least one therapeutic ultrasound transducer in view of its focusing properties, so that the at least one therapeutic ultrasound transducer by means of said optical navigating device can be positioned such that said temperature focus appears in the disc to be treated.

29. Method according to claim 28, further comprising the step of calculating, by means of the computer provided with at least one computer program, the heating effect of the ultrasonic field of the at least one therapeutic ultrasound transducer in its temperature focus based on the acoustic properties determined by the diagnostic ultrasound transducer.

30. Method according to claim 22, further comprising the step of determining the position of the anatomic structure of the treatment area displayed in a monitor by means of a calibrating device with markers comprised in a X-ray camera.

31. Method according to claim 30, further comprising the step of displaying, by means of the monitor, two X-ray photographs of said anatomic structure taken with the X-ray camera from two different locations.

32. Method according to claim 22, further comprising the step of determining, by means of the diagnostic ultrasound transducer, the thickness of different layers of said tissue for determining the acoustic properties thereof.

33. Method according to claim 22, further comprising the step of producing, by means of the diagnostic ultrasound transducer, a picture or image of said tissue.

34. Method according to claim 22, further comprising the step of manually positioning the at least one therapeutic ultrasound transducer by means of calculated determination of the temperature focus of the ultrasonic field of said at least one therapeutic ultrasound transducer relative to the transmitter element of the at least one therapeutic ultrasound transducer.

35. Method according to claim 22, further comprising the step of positioning the at least one therapeutic ultrasound transducer, by means of a positioning device, relative to the disc to be treated.

36. Method according to claim 22, further comprising the step of providing a temperature above 45° C. in the temperature focus of the at least one therapeutic ultrasound transducer.

37. Method according to claim 22, further comprising the step of providing a calibrating device for calibrating the effect emitted by the at least one therapeutic ultrasound transducer in the temperature focus of said at least one therapeutic ultrasound transducer and/or the position of said temperature focus relative to the transmitter element of the at least one therapeutic ultrasound transducer.

* * * * *

UNITED STATES PATENT AND TRADEMARK OFFICE
CERTIFICATE OF CORRECTION

| | | |
|---|---|---|
| PATENT NO. | : 7,387,613 B2 | Page 1 of 1 |
| APPLICATION NO. | : 10/333159 | |
| DATED | : June 17, 2008 | |
| INVENTOR(S) | : Lars Ake Alvar Lidgren | |

It is certified that error appears in the above-identified patent and that said Letters Patent is hereby corrected as shown below:

Title page, item (30) Foreign Application Priority Data:

Delete "July 17, 2001" and insert -- July 17, 2000 --.

Signed and Sealed this

Second Day of June, 2009

JOHN DOLL
*Acting Director of the United States Patent and Trademark Office*